United States Patent [19]

Dohi et al.

[11] Patent Number: 5,578,324
[45] Date of Patent: Nov. 26, 1996

[54] PEPTIDE PROTEINACEOUS DRUG NASAL POWDER COMPOSITION

[75] Inventors: Masahiko Dohi, Hino; Yoshihisa Nishibe, Fuchu; Yuji Makino; Yoshiki Suzuki, both of Hino, all of Japan

[73] Assignee: Teijin Limited, Osaka, Japan

[21] Appl. No.: 407,000

[22] PCT Filed: Jul. 29, 1994

[86] PCT No.: PCT/JP94/01257

§ 371 Date: Mar. 29, 1995

§ 102(e) Date: Mar. 29, 1995

[87] PCT Pub. No.: WO95/03818

PCT Pub. Date: Feb. 9, 1995

[30] Foreign Application Priority Data

| Jul. 30, 1993 | [JP] | Japan | 5-206922 |
| Aug. 30, 1993 | [JP] | Japan | 5-235841 |
| Jan. 12, 1994 | [JP] | Japan | 6-001644 |

[51] Int. Cl.⁶ ............................ A61K 9/50
[52] U.S. Cl. ................ 424/499; 424/490; 424/489
[58] Field of Search ................. 424/499, 490, 424/489

[56] References Cited

FOREIGN PATENT DOCUMENTS 6172199 of 1995 Japan.

Primary Examiner—Paul R. Michl
Assistant Examiner—William E. Benston, Jr.
Attorney, Agent, or Firm—Sughrue, Mion, Zinn, Macpeak & Seas

[57] ABSTRACT

A peptide proteinaceous drug nasal powder composition containing (i) an absorption accelerant comprised of a compound, or its salt, having in its molecule a group expressed by the formula (I):

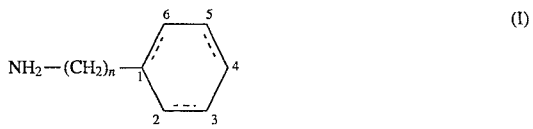

wherein, indicates a cyclohexane ring or a benzene ring which may be substituted at least one of its 3-position, 4-position, and 5-position and n is an integer of 1 to 3 and (ii) a therapeutically effective amount of a peptide proteinaceous drug.

18 Claims, 3 Drawing Sheets

SEQUENCE LISTING ( 1 ) GENERAL INFORMATION:

( i i i ) NUMBER OF SEQUENCES: 6

( 2 ) INFORMATION FOR SEQ ID NO: 1:

( i ) SEQUENCE CHARACTERISTICS:
    ( A ) LENGTH: 11 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO: 1:

Cys Ser Asn Leu Ser Thr Cys Val Leu Gly Lys
  1               5                   10

( 2 ) INFORMATION FOR SEQ ID NO: 2:

( i ) SEQUENCE CHARACTERISTICS:
    ( A ) LENGTH: 21 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO: 2:

Leu Ser Gln Glu Leu His Lys Leu Gln Thr Tyr Pro Arg Thr Asn
  1               5                   10                  15
  Thr Gly Ser Gly Thr Pro
                  20

( 2 ) INFORMATION FOR SEQ ID NO: 3:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear (ii) MOLECULE TYPE: peptide (xi) SEQUENCE DESCRIPTION: SEQ ID NO: 3:

Leu Ser Gln Glu Leu His Lys
1               5

(2) INFORMATION FOR SEQ ID NO: 4:

(i) SEQUENCE CHARACTERISTICS:
    (A) LENGTH: 6 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO: 4:

Leu Gln Thr Tyr Pro Arg
1               5

(2) INFORMATION FOR SEQ ID NO: 5:

(i) SEQUENCE CHARACTERISTICS:
    (A) LENGTH: 8 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO: 5:

Thr Asn Thr Gly Ser Gly Thr Pro
1               5

(2) INFORMATION FOR SEQ ID NO: 6:

(i) SEQUENCE CHARACTERISTICS:
    (A) LENGTH: 4 amino acids
    (B) TYPE: amino acid
    (C) STRANDEDNESS: single
    (D) TOPOLOGY: linear

(ii) MOLECULE TYPE: peptide (xi) SEQUENCE DESCRIPTION: SEQ ID NO: 6:

Ala Ala Pro Phe
1

PEPTIDE PROTEINACEOUS DRUG NASAL POWDER COMPOSITION

TECHNICAL FIELD

The present invention relates to a peptide proteinaceous drug nasal powder composition having an improved absorbency. More specifically, it relates to a peptide proteinaceous drug nasal powder composition, which is improved in absorption from the mucous membrane of the nasal cavity to the blood stream of the entire body by suppression of the decomposition of the peptide proteinaceous drug administered to the nasal cavity by an absorption accelerant having specified groups.

BACKGROUND ART

Along with the progress in biotechnology in recent years, there have been a succession of discoveries of peptide roteinaceous compounds having physiological activity. Production of these compounds has become easy as well. Many of these peptide proteinaceous drugs are used only as injections due to the low level of their stability and absorbency. However, these drugs are preferably administered in multiple dosages for therapeutic reasons. Administration by injection in this case places a burden on the patient due to the pain to the patient and the need for visiting a hospital.

Therefore, other various methods of administration have been examined as non-invasive methods of administration of peptide proteinaceous drugs to take the place of injections, for example, the method of rectal administration by suppositories (J. Pharma., 33 334 (1981)), bronchial administration (Diabetes 20 552 (1971)), instillation administration (Abstracts of Diabetes Society 237 (1964)), etc. All of these methods, however, are hard to commercialize due to the difficulties that higher dosages are required than with injections and the absorption tends to fluctuate.

On the other hand, the nasal cavity has a well developed system of blood vessels in the mesothelium layer and is able to absorb a drug quickly and with little variation. Due to these advantages, the nasal administration method has come into attention. At the present time, however, sufficient absorption cannot be obtained, and therefore, various studies are under way to raise the absorbency.

For example, Nolte et al. (Hormone Metabolic Research 22, 170–174, 1990), Moses (Pharmaceutisch Week-blad-Scientific Edition 10, 45–46, 1988), Bruce et al. (Diabetic Medicine 8, 366–370,1991), etc. report on nasal administration of insulin containing sodium glycocholate or sodium taurofusidate as absorption accelerants. These preparations containing absorption accelerants, however, have problems with irritation to the nasal mucous membrane, and therefore, have not been commercialized.

As the major causes for the low absorbency of a peptide proteinaceous drug from the nasal mucous membrane, Illum (Trends Biotechnol 9, 284–289, 1991), W. A. Lee (Biopharm. Manuf. 1, 30–37, 1988), Edman (Advanced Drug Delivery Reviews 8, 165–177, 1992), etc. have mentioned the low level of drug permeability into the mucous membrane, the elimination of the drug by ciliary movement, and the degradation of the drug by the protease in the nasal cavity.

Among these, as a major discovery relating to the protease in the nasal cavity, O'Hagan et al. (Pharm. Res. 7, 772 (1990)), Hussain et al. (Pharm. Res. 6, 186 (1989)), showed by animal experiments using rats and sheep that the nasal absorption of insulin, growth hormone, enkephalin, and other peptide proteinaceous drugs is improved by administration together with amastatin, bestatin, α-aminoboronic acid, or other aminopeptidase inhibitors.

Further, Illum et al. (Japanese National Disclosure (Kohyo) No. 2-503915) mentioned that effective protease inhibitors for nasal preparations in studies of rats, rabbits, and sheep were actinonin, amastatin, bestatin, chloroacetyl-HO-Leu-Ala-Gly-NH$_2$, diprotin A and B, evelactone A and B, E- 64, H-(tBu)-Phe-Pro-OH, kallikrein inhibitor I, chymotrypsin inhibitor I, trypsin inhibitor III- 0, leupeptin, pepstatin, phosphoramidone, aprotinin, chymostatin, and benzamidine.

Further, Morimoto et al. (111 and 112 Ann. Meetings of JPN Pharm, Soc.) showed by by animal experiments using rats that the nasal absorbency of salmon calcitonin was improved by administering it with aprotinin, TAME (tosyl arginine methyl ester), which was a synthetic substrate of trypsin, or other trypsin inhibitors.

Further, the present inventors confirmed by animal experiments using rabbits that in the nasal cavity of rabbits, salmon calcitonin, LHRH, insulin, and other peptide proteinaceous drugs were cleaved at the C terminal of the Leu in their primary structures and that the nasal absorbency of these is improved by administering them with a chymotrypsin inhibitor (for example, see Japanese Patent Application No. 5-130993 i.e., Japanese Unexamined Patent Publication No. 6-321804.

These findings, however, were all based on animal experiments using rats, sheep, and rabbits and the significance for humans is unclear. Accordingly, at the present time, it is not clear if the methods for improving the nasal absorbency of peptide proteinaceous drugs in rats, sheep, rabbits, and other animals would be effective for humans.

DISCLOSURE OF INVENTION

Accordingly, the present invention provides a peptide proteinaceous drug nasal powder composition which, by combined use of a protease inhibitor, suppresses the degradation of the peptide proteinaceous drug in the human nasal cavity by the action of the enzyme, is improved in the nasal absorbency, and is safe to the body.

In accordance with the present invention, there is provided a peptide proteinaceous drug nasal powder composition comprising (i) an absorption accelerant comprising a compound, or its salt, having in its molecule a group expressed by the formula (I):

(wherein, indicates a cyclohexane ring or a benzene ring which may be substituted at least one of its 3-position, 4-position, and 5-position and n is an integer of 1 to 3) and (ii) a therapeutically effective amount of a peptide proteinaceous drug.

BRIEF DESCRIPTION OF THE DRAWINGS

The present invention will now be explained in further detail with reference to the drawings; wherein.

BEST MODE FOR CARRYING OUT THE INVENTION

As mentioned above, the present inventors found that a compound having the specific formula (I) suppressed the degradation of peptide proteinaceous drugs in the human nasal cavity and improves the nasal absorbency.

It should be noted that, as is clear from the later Reference Experiments and Examples, the compound having the above-mentioned formula (I), that is, the absorption accelerant for providing a peptide proteinaceous drug preparation which suppresses the degradation of peptide proteinaceous drug in the human nasal cavity by the action of the protease and improves the nasal absorbency, as aimed at by the present invention, may be said to be a compound where the aminomethyl group, aminoethyl group, and aminopropyl group have attached to them a cyclohexane ring or benzene ring that cannot cover these groups spatially due to the intermolecular electrostatic interaction or rigidity etc. Accordingly, also included in the absorption accelerant of the present invention are compounds in which the substituents and cyclohexane and benzene are substituted by other substituents, for example, chain (straight chain, branched) or cyclic saturated or unsaturated hydrocarbon groups etc. to the extent to which it is naturally assumed that these groups will not be covered spatially due to the intermolecular electrostatic interaction or rigidity etc.

That is, the compound of formula (I) has a $NH_2$-$(CH_2)_n$- group. It is essential that this is bonded together with a cyclohexane ring or benzene ring. With just this structure, the cyclohexane ring or benzene ring may have a substituent at the 3-, 4-, and/or 5-position three-dimensionally separated from the $NH_2$-$(CH_2)_n$-group. The substituent is not particularly limited so long as it is a group which is stable as a preparation in the case of being made a powder and which poses no safety problem in terms of irritation etc. when administered to a human patient. More specifically, the compound having the group of the structure of formula (I) may be expressed by the following general formula (II):

wherein, n is an integer of 1 to 3, preferably 1 to 2, and $R^1$, $R^2$ and $R^3$ are, independently, a group selected from a hydrogen atom, phosphoric acid group, cyano group, COOR, COR, OR', $S(O)_pR'$, NR'R", carbamoyl group, $SO_2NH_2$, and substitutable $C_1$-$C_{20}$ hydrocarbon group, wherein R represents a hydrogen atom; $C_1$-$C_6$ lower alkyl group which may be substituted; or $CH_2CH_2COOR'$, R' and R" epresent, independently, a hydrogen atom; $C_1$-$C_6$ lower alkyl group which may be substituted, phenyl group which may be substituted, or $C_7$-$C_8$ aralkyl group which may be substituted, and p is an integer of 0 to 3.

In these $R^1$ to $R^3$, as the $C_1$-$C_6$ lower alkyl group, mention may be made of a methyl group, ethyl group, n-propyl group, i-propyl group, n-butyl group, i-butyl group, s-butyl group, t-butyl group, n-pentyl group, n-hexyl group, cyclopropyl group, and other straight chain or branched chain or cyclic alkyl groups. Among these, a methyl group, ethyl group, n-butyl group, and other $C_1$-$C_4$ lower alkyl groups may be mentioned as being preferable. Further, as the $C_7$-$C_8$ aralkyl group, mention may be made of a benzyl group and phenylethyl group.

Further, the $C_1$-$C_{20}$ hydrocarbon group means a saturated or unsaturated chain (straight chain or branched) or cyclic hydrocarbon group. For example, mention may be made of those similar to those illustrated as the $C_1$-$C_6$ lower alkyl group and those which, when unsaturated, have one or more double bonds and/or triple bounds, such as a heptyl group, decyl group, eicosyl group, 2,2-dimethyloctyl group, cyclohexylbutyl group, propenyl group, isopentenyl group, 8-heptadecenyl group, and 8,11-heptadecadienyl group. As the $C_1$-$C_{20}$ hydrocarbon group, preferably, mention may be made of a $C_1$-$C_{15}$ hydrocarbon group, more preferably a $C_1$-$C_{10}$ hydrocarbon group.

As a specific example of the COOR of the $R^1$ to $R^3$, mention may be made of a carboxyl group, methoxycarbonyl group, ethoxycarbonyl group, hexyloxycarbonyl group, and and as a specific example of the COR, mention may be made of formyl group, acetyl group, propionyl group, and Further, as specific examples of the $S(O)_pR'$, mention may be made of a thiol group, sulfenic acid group, sulfinic acid group, sulfonic acid group, methylthiol group, isopropyl thiol group, isopropyl sulfinyl group, isopropyl sulfonyl group, pentyl sulfonyl group, phenyl thiol group, phenyl sulfonyl group, etc. Further, as specific examples of NR'R", mention may be made of an amine group, dimethyl amine group, diethyl amine group, benzyl amine group, phenethyl amine group, etc.

Further, as specific examples of the OR', mention may be made of a hydroxyl group, methoxyl group, ethoxyl group, (n-, i-) propoxyl group, (n-, i-, s-, t-) butoxyl group, hexyloxyl group, cyclopropylmethyloxyl group, phenyloxyl group, phenethylloxyl group, etc.

The $R^1$ to $R^3$ of the present invention may, when having a $C_1-C_{20}$ hydrocarbon group; $C_1-C_6$ lower alkyl group, phenyl group, or $C_7-C_8$ aralkyl group, further have substituents at these groups. As such substituents, mention may be made of the phosphoric acid group, cyano group, COOR, COR, OR', $S(O)_pR'$, NR'R", carbamoyl group, and $SO_2NH_2$ exemplified as $R^1$ to $R^3$.

As the absorption accelerant of the present invention, mention may be made of the compounds in formula (I) or (II), wherein n=1 or 2 mentioned as preferable.

As the substituent on the cyclohexane ring or benzene ring in the above-mentioned formula (I) or (II), mention may be made of a substituent selected from COOR, COR, OR', $SO_2NH_2$ and a $C_1-C_{10}$ hydrocarbon group among those illustrated as $R^1$ to $R^3$.

In particular, in the above-mentioned formula (I) or (II), when the cyclic structure is a cyclohexane ring and n=1, preferable mention may be made of a compound wherein the substituent is a group selected from among the group comprising a hydrogen atom, COOR, and COR. In particular, preferable mention may be made of a group selected from the group comprising a hydrogen atom, carboxyl group, In this case, specific mention may be made of the case where as the substituents as $R^1$ to $R^3$, $R^1$ to $R^3$ are hydrogen atoms or $R^1$ and $R^3$ are hydrogen atoms and $R^2$ is a group other than a hydrogen atom.

Further, when the cyclic structure is a benzene ring and n=1 or 2 in the above-mentioned formula (I) or (II), preferable mention may be made of a compound wherein the substituent is a group selected from the group comprising a hydrogen atom, $SO_2NH_2$, and OR', in particular, mention may be made of the case where n=1 and the substituent is a group selected from a hydrogen atom, carboxyl group, and $SO_2NH_2$ (sulfamine) group or n=2 and the substituent is a hydrogen atom or hydroxyl group. In this case, specific mention may be made of the case where as the substituents as $R^1$ to $R^3$, when n=1, $R^1$ to $R^3$ are hydrogen atoms or $R^1$ and $R^3$ are hydrogen atoms and $R^2$ is a carboxyl group or $SO_2NH_2$ group or, when n=2, $R^1$ is a hydrogen atom and $R^2$ and $R^3$ are hydroxyl groups.

As further preferable examples of the compounds having the formula (I), mention may be made for example of cyclohexane methylamine, benzylamine, p- aminomethyl benzoic acid, tranexamic acid, rotraxate hydrochloride, cetraxate hydrochloride, mafenide acetate, dopamine hydrochloride, and their derivatives and acid addition salts and other salts.

Tranexamic acid has been known as a hemostyptic and is used at the time of abnormal bleeding caused by systemic hyperfibrinolysis. Its safety in the body has already been confirmed.

Rotraxate hydrochloride is known as a drug which has, as pharmaceutical actions, (1) an action of increasing the blood flow in the gastric mucous membrane and (2) an action of promoting the secretion of bicarbonate ion in the gastric mucous membrane and exhibits an anti-ulcer action that reinforces the function of protection of the gastric mucous membrane (see Japanese Examined Patent Publication (Kokoku) No. 60-36418).

Cetraxate hydrochloride is a drug which is used clinically for adaptation symptoms such as (1) lesions in the gastric mucous membrane (sores, bleeding, reddening, edema) due to the following ailments: acute gastritis and the acute exacerbated phase of chronic gastritis and (2) stomach ulcers (Nihon Iyakuhinshu 1993, p. 581, Yakuji Jihosha).

Mafenide acetate has been known in the past as an antibacterial agent and is effective for infection of wound surfaces by bacteria at the time of burns (Nihon Yakuhin Yoran, 5th edition, p. 1140, Yakuji Jihosha).

Dopamine hydrochloride is a drug which is used clinically for adaptation symptoms such as (1) acute circulatory insufficiency (cardiogenic shock, hemorraghic shock) and (2) acute circulatory insufficiency conditions (Nihon Iyakuhinshu 1993, p. 772, Yakuji Jihosha).

However, no method of use for improving the absorption by nasal powders of peptide proteinaceous drugs has been known for tranexamic acid, rotraxate hydrochloride, cetraxate hydrochloride, mafenide acetate, dopamine hydrochloride, and other compounds of the present invention. Further, they are not included in the protease inhibitors mentioned in the patent relating to nasal preparations of Illum et al.

Tranexamic acid suppresses the enzymatic degradation of the peptide proteinaceous drug in the human nasal cavity, so it could be guessed that there is plasmin present in the human nasal cavity and that the plasmin cleaves down the peptide proteinaceous drug, but in the present invention the plasmin activity is low and, also, no effect of promoting nasal absorption was observed in by the ε-amino caproic acid, which is a kind of plasmin inhibitor, so the possibility of plasmin playing a major part in the degradation of the peptide proteinaceous drug is denied.

Further, a trypsin-like enzyme is present in the human nasal cavity. The peptide proteinaceous drug administered in the nasal cavity is mainly cleaved by this enzyme. It is possible to improve the nasal absorbency of peptide proteinaceous drugs by administering a trypsin inhibitor in the human nasal cavity at the same time. However, tranexamic acid, rotraxate hydrochloride, cetraxate hydrochloride, mafenide acetate, dopamine hydrochloride, and other compounds of the present invention have no trypsin inhibiting activity, but maintain a higher effect that the effect of promotion of the rate of nasal absorption of a trypsin inhibitor.

In other words, a trypsin-like enzyme exists in the human nasal cavity and the peptide proteinaceous drug administered in the nasal cavity is mainly broken down by that enzyme, but it is believed that the enzyme is restrained more effectively than a trypsin inhibitor by the compound of the present invention, such as tranexamic acid, rotraxate hydrochloride, cetraxate hydrochloride, mafenide acetate, dopamine hydrochloride, etc.

Accordingly, tranexamic acid, rotraxate hydrochloride, cetraxate hydrochloride, mafenide acetate, dopamine hydrochloride, and other compounds of the present invention can improve the stability of peptide proteinaceous drugs in the human nasal cavity and, accordingly, by administering them together with peptide proteinaceous drugs in the nasal cavity, can improve the nasal absorbency of the peptide proteinaceous drugs.

The tranexamic acid used herein means trans-4-(aminomethyl) cyclohexane carboxylic acid, but in the present invention use may also be made of the cis-form, namely, cis-4-(aminomethyl) cyclohexane carboxylic acid.

Further, the rotraxate hydrochloride means a hydrochloride of 3-((p-(trans-4-aminomethylcyclohexylcarbonyl)phenyl)) propionic acid, but in the present invention, use may also be made of the cis-form, namely, a hydrochloride of 3-(p-(cis-4-aminomethylcyclohexylcarbonyl)phenyl) propionic acid and also other pharmaceutically allowable salts.

Further, the cetraxate hydrochloride means a hydrochloride of trans-(4-aminomethyl) cyclohexane carboxylic acid p-(2-carboxyethyl)phenyl ester, but in the present invention, use may also be made of the cis-form, namely, cis-(4-aminomethyl) cyclohexane carboxylic acid p-(2-carboxy ethyl)phenyl ester and also other different pharmaceutically allowable salts.

Further, the mafenide acetate means an acetate of 4-(aminomethyl) benzenesulfamine, but in the present invention, use may also be made of other pharmaceutically allowable salts.

Further, the dopamine hydrochloride means a hydrochloride of 4-(2-aminoethyl)-1,2 benzenediol, but in the present invention, use may also be made of other pharmaceutically allowable salts.

The salt of the compound of the above formula (I) or (II) of the present invention means, for example, an acid addition salt, metal salt, or other pharmaceutically allowable salt. As a metal salt, mention may be made of a sodium salt, potassium salt, and other alkali metal salt.

It should be noted that the acid of the acid addition salt is not limited so long as it gives a pharmaceutically allowable acid addition salt. For example, mention may be made of hydrochloric acid, sulfuric acid, phosphoric acid, and other inorganic acids and for example acetic acid, citric acid, tartaric acid, maleic acid, fumaric acid, and other organic acids, etc. In particular, preferable mention may be made of hydrochloric acid, acetic acid, etc.

In the present invention, as the peptide proteinaceous drug, mention may be made of at least one type of peptide proteinaceous drug selected from the group comprising calcitonins, somatostatin (GIF) and its derivatives, parathyroid hormones (PTH), substance P, platelet derived growth factors (PDGF), galanin, gastrin, neurokinins, interleukins, neurotensin, endo serine, growth hormone-releasing hormone (GHRH) and its derivatives, growth hormone releasing factor (GRF), luteinizing hormone-releasing hormone (LHRH) and its derivative, enkephalin and its derivatives, secretin, bradykinin and its derivatives, adrenocorticotrophic hormone (ACTH) and its derivatives, insulins, glucagon, insulin growth factor (IGF), calcitonin gene related peptide (CGRP), vasopressin and its derivatives, atrial natrium peptide (ANP), erythropoietin, granulocyte colony stimuli factor (G-CSF), and macrophage colony stimuli factor (M-CSF).

Among these, as preferable peptide proteinaceous drugs of the present invention, mention may be made of calcitonin, somatostatin (GIF), growth hormone releasing hormone (GHRH), luteinizing hormone-releasing hormone (LHRH), parathyroid hormone (PTH), or their derivatives.

Among these drugs, calcitonin is a peptide hormone which regulates the metabolism of calcium in the body. It works to obstruct the absorption of calcium in the bones and to cause the reabsorption of calcium released from the kidneys. There are known salmon calcitonin, eel calcitonin, human calcitonin, pig calcitonin, chicken calcitonin, bovine calcitonin, sheep calcitonin, rat calcitonin, etc. In the present invention, use may be made of the derivatives of these calcitonins, for example, elcatonin and other synthetic calcitonin and genetically engineered calcitonin.

Somatostatin (GIF) is a peptide comprised of 14 amino acid residues which act on the pituitary of vertebrates to suppress the release of GH and TSH and PRL and suppress secretion of gastrin, motilin, secretin, digestive enzymes, gastric acids, etc. in the gastropancreatic system. There are known human, rat, sheep, dove, angler, and pig types. As derivatives of somatostatin, there are known for example ones like octoreotide acetate and other synthetic somatostatins wherein part of the amino acids are substituted with the D-form and several amino acids are removed to give 6 to 7 amino acid residues. In the present invention, each of these may also be used.

The luteinizing hormone-releasing hormone (LHRH) is a peptide which acts on the GTH cells of the anterior pituitary of vertebrates to cause the release of LH and FSH. Human, pig, chicken, salmon, and eel types are known. As the derivatives, there are known for example [D-Ser(t-Bu)$^6$, des-Gly$^{10}$ ethylamide] LHRH, [D-Ala-3(2-Naphtyl)$^6$] LHRH, [D-Leu$^6$, des-Gly$^{10}$ ethylamide] LHRH, [D-Ser(t-Bu)$^6$, aza-Gly$^{10}$] LHRH, [N-Ac-D-Nal(2)$^1$, DpFPhe$^2$, D-Pal(3)$^3$, Lys(Nic)$^5$, D-Lys(Nic)$^6$, Lys(iPr)$^8$, D-Ala$^{10}$] LHRH, and other synthetic LHRH and others with the 6-position Gly substituted with a D-form and others with the C-terminal glysine-amide substituted with alkylamine.

The growth hormone releasing hormone (GHRH) is a peptide which is comprised of 43 to 44 amino acid residues which act on the anterior pituitary of mammals and cause the release of growth hormones (GH). There are known human, rat, bovine, sheep, and pig types. As the derivatives, there are known ones with the C-terminal taken and made (1–29)-NH$_2$ etc. In the present invention, each of these may also be used.

Parathyroid hormone (PTH) is a peptide which is comprised of 84 amino acid residues which act on bone and kidney and promote reabsorption of Ca$^{2+}$. As its derivatives, there are known PTH$_{1-34}$NH$_2$, which is comprised of 1 to 34 amino acid residues of the N terminal etc. In the present invention, each of these may also be used.

As the combination of the absorption accelerant of the present invention and the peptide proteinaceous drug, mention may be made of the absorption accelerant having the above formula (I) or expressed by the formula (II) and a peptide proteinaceous drug. Among these, as preferable combinations, mention may be made of (1) an absorption accelerant of tranexamic acid, rotraxate hydrochloride or cetraxate hydrochloride and, in this case, a peptide proteinaceous drug of, for example, the above illustrated salmon calcitonin and other calcitonins, human somatostatin and other somatostatins, growth hormone acceleration hormones, and their derivatives, (2) an absorption accelerant of mafenide or its pharmaceutically allowable acid addition salts, in particular, mafenide acetate, and, in this case, a peptide proteinaceous drug of, for example, the above illustrated salmon calcitonin and other calcitonins, human somatostatin and other somatostatins, and their derivatives, and (3) an absorption accelerant of dopamine or its pharmaceutically allowable acid addition salts, in particular, dopamic hydrochloride, and, in this case, a peptide proteinaceous drug of, for example, the above-illustrated salmon calcitonin and other calcitonins, human somatostatin and other somatostatins, and their derivatives.

The amount of the peptide proteinaceous drug in the present invention is the therapeutically effective amount. The amount is specific to the different types of peptide proteinaceous drug. The therapeutically effective amount is usually preferably the same amount 1 to 20 times the amount of the peptide proteinaceous drug administered by injection, more preferably 2 to 10 times the amount.

On the other hand, the amount of the absorption accelerant of the present invention is preferably approximately 0.1–10 parts by weight based on 1 part by weight of the therapeutically effective amount of the peptide proteinaceous drug, more preferably approximately 1 to 5 parts by weight, still more preferably 1 to 3 parts by weight. The amounts and ratio in the case of mixing two or more types of absorption accelerants are not particularly limited, but the total amount is preferably in this range.

The peptide proteinaceous drug nasal powder of the present invention is produced by mixing one or more types of a fine powder peptide proteinaceous drug and the absorption accelerant of the present invention, for example, a water absorbing and water-insoluble base. The mixing is performed using a mortar, high speed mixer, or other usual mixer. The water-absorbing and water-insoluble base spoken of here means something which has absorbency and insolubility on human nasal mucous membrane or in an environment close to that, that is, with respect to water of a pH of about 7.4 and a temperature of about 36° C. to about 37° C.

As preferable specific examples, mention may be made of water-absorbing and water-insoluble cellulose such as microcrystalline cellulose, α-cellulose, cross-linked sodium carboxymethylcellulose, and their derivatives; water-absorbing and water-insoluble hydroxypropyl starch, carboxymethyl starch, cross-linked starch, amylose, amylopectin, pectin and their derivatives; water-absorbing and water-insoluble gum such as arabia gum, tragacanth gum, glucomannan and their derivatives; and cross-linked vinyl polymers such as polyvinylpolypyridone, cross-linked polyacrylic acid and its salt, cross-linked polyvinyl alcohol, polyhydroxyethylmethacrylate and their derivatives. Among these, water-absorbing and water-insoluble cellulose is preferable, in particular, microcrystalline cellulose and its derivative are desirable.

It is also possible to add to this powder, in addition to the one or more types of peptide proteinaceous drugs, the absorption accelerant of the present invention, and above-mentioned substrate, according to requirement, a known lubricant, preservative, antiseptic, deodorant, etc.

As a lubricant, for example, mention may be made of talc, stearic acid and its salts, etc.; as a colorant, for example, mention may be made of copper chlorophyll, β-carotene, red No. 2, blue No. 1, etc.; as a preservative, for example, mention may be made of stearic acid, ascorbic acid stearate, etc.; as an antiseptic, for example, mention may be made of benzylkonium chloride and other quaternary ammonium compounds, paraoxybenzoic acid esters, phenols, chlorobutanol, etc.; and as deodorant, mention may be made for example of menthol, citrus fragrances, etc.

The peptide proteinaceous drug nasal powder of the present invention is usually administered in the nasal cavity by the following method. That is, a capsule filled with the powder to set for example in an exclusive spray apparatus possessing a needle, the needle is made to penetrate it to make fine holes at the top and bottom of the capsule, then air is fed by a rubber ball etc. to make the powder spray out.

EXAMPLES

The present invention will now be explained in more detail in accordance with the Reference Experiments and Examples, but of course the present invention is not limited to these Examples.

Reference Experiment 1

(1) A homogenate solution was prepared from human nasal mucosa to give 1 mg/ml protein. To 0.5 ml portions of this homogenate were added 0.5 ml portions of an aqueous solution of salmon calcitonin (0.1 mg/ml). The results were incubated at 37° C., then the degradation fragments of the salmon calcitonin in the reaction liquid were separated by HPLC (L-6200 series (made by Hitachi, Ltd.) by 100% $H_2O$ from 0 to 5 minutes, 100% to 50% $H_2O$ and 0 to 50% acetonitrile from 5 to 55 minutes). The amino acid sequences of the separated fragments were determined by an amino-acid sequencer (made by Applied Biosystems). The first fragment of salmon calcitonin in human nasal mucosal homogenate are shown to Table 1.

TABLE 1

| Degradation Fragments in Human Nasal Mucosal Membrane Homogenate | |
| --- | --- |
| Salmon calcitonin fragment 1 (SEQ ID NO: 1) | Cys—Ser—Asn—Leu—Ser—Thr—Cys—Val—Leu—Gly—Lys |
| Salmon calcitonin fragment 2 (SEQ ID NO. 2) | Leu—Ser—Gln—Glu—Leu—His—Lys—Leu—Gln—Thr—Tyr—Pro—Arg—Thr—Asn—Thr—Gly—Ser—Gly—Thr—Pro—NH$_2$ |

As shown in Table 1, the C end side of Lys of the peptide proteinaceous drug is first cleaved in a human nasal mucosal homogenate. From this, it is guessed that the protease which first cleaves the peptide proteinaceous drug in the human nasal cavity is a trypsin-like enzyme.

A refined trypsin (made by Wako Pure Chemical Industry) was used, instead of the human nasal mucosal homogenate solution, in the same procedures followed as in (1) to separate the degradation fragments of salmon calcitonin in the reaction liquid by HPLC. In the same way as (1), the amino acid sequence was determined by an amino-acid sequencer. The results are shown in Table 2.

TABLE 2

| Salmon Calcitonin Degradation Fragments by Trypsin | |
| --- | --- |
| Fragment 1 (SEQ ID NO: 2) | Cys—Ser—Asn—Leu—Ser—Thr—Cys—Val—Leu—Gly—Lys |
| Fragment 2 (SEQ ID NO: 3) | Leu—Ser—Gln—Glu—Leu—His—Lys |
| Fragment 3 (SEQ ID NO: 4) | Leu—Gln—Thr—Tyr—Pro—Arg |
| Fragment 4 (SEQ ID NO: 5) | Thr—Asn—Thr—Gly—Ser—Gly—Thr—Pro—NH$_2$ |

As shown in Table 2, the degradation fragments of salmon calcitonin caused by refined trypsin are different from the degradation fragments of salmon calcitonin of Table 1. From this, it is guessed that the trypsin-like enzyme present in the human nasal cavity is not trypsin itself.

Reference Experiment 2

A homogenate solution was prepared from human nasal mucosa to give 1 mg/ml of protein. Next, synthesis substrates corresponding to the various proteases shown in Table 1 were added to 0.5 ml portions of the homogenate solution to give 0.1 mM concentrations. The results were incubated at 37° C. The amounts of the substrates remaining after a predetermined time were measured by HPLC to find the amounts of substrates cleaved and find the activity of the various proteases. The results are shown in Table 3.

TABLE 3

Activity of Protease in Human Nasal Mucosal Homogenate

| Synthesized substrate | Corresponding protease | Activity (nM/h/mg protein) |
| --- | --- | --- |
| Boc—Gln—Ala—Arg—MCA | Trypsin | 525 |
| Boc—Val—Pro—Arg—MCA | α-Thrombin | 269 |
| Boc—Phe—Ser—Arg—MCA | Trypsin | 250 |
| Pro—Phe—Arg—MCA | Kallikrein | 85 |
| Suc—Ala—Ala—Pro—Phe—MCA (SEQ ID NO: 6) | Chymotrypsin | 24 |
| Boc—Glu—Lys—Lys—MCA | Plasmin | 14 |
| Suc—Ala—Ala—Ala—MCA | Elastase | 3 |
| Bz—Arg—MCA | Trypsin | 1 |

In the synthesis substrates, Boc means a t-Butyloxycarbonyl group, Suc means a Succinyl group, Bz means a Benzyl group, and MCA means 4-Methyl-Coumaryl-7-Amide.

ants of the present invention were added, and the results were incubated at 37° C. The amounts of the peptide proteinaceous drug not yet cleaved after a predetermined time were measured by HPLC to find the amounts of decomposition. The inhibition rates were calculated by the following formula. The results are shown in Table 4.

Inhibition rate (%)=(A-B)/A×100

A: Amount of peptide proteinaceous drug cleaved when enzyme inhibitor or absorption accelerant of present invention is not added to homogenate B: Amount of peptide proteinaceous drug cleaved when enzyme inhibitor or absorption accelerant of present invention is added to homogenate ε-ACA: ε-Amino caproic acid
SCT: Salmon calcitonin
INS: Insulin
GIF: Somatostatin
ACTH: Adrenocorticotropic hormone
PTH: Parathyroid hormone
CGRP: Calcitonin gene related peptide
GLU: Glucogon
PDGF: Platelet-derived growth factor
S.p: Substance P
GHRH: Growth hormone releasing hormone
LHRH: Luteinizing hormone releasing hormone

TABLE 4

Inhibitory Effect on Degradation of Peptide Proteinaceous Drug in Human Nasal Mucosal Homogenate By Various Protease Inhibitors

| Inhibitor (corresponding enzyme) or accelerant of present invention | Inhibitor (%) | | | | | | | | | | |
| --- | --- | --- | --- | --- | --- | --- | --- | --- | --- | --- | --- |
| | SCT | INS | GIF | ACTH | PTH | CGRP | GLU | PDGF | S.p | GHRH | LHRH |
| Aprotinin (trypsin) | 14 | 18 | 22 | 11 | 15 | 20 | 25 | 7 | 25 | 15 | 15 |
| Gabexate (trypsin) | 53 | 46 | 56 | 48 | 44 | 49 | 56 | 43 | 40 | 40 | 27 |
| Chymostatin (chymotrypsin) | 38 | 22 | 25 | 12 | 15 | 23 | 35 | 10 | 15 | 25 | 16 |
| TPCK (chymotrypsin) | 0 | 7 | 11 | 8 | 10 | 0 | 5 | 3 | 10 | 0 | 5 |
| Pepstatin (pepsin) | 10 | 15 | 0 | 4 | 10 | 10 | 8 | 0 | 0 | 0 | 0 |
| ε-ACA (plasmin) | 0 | 0 | 0 | 0 | 0 | 0 | 0 | 0 | 0 | 0 | 0 |
| Thiorphan (metalloprotease) | 0 | 0 | 0 | 0 | 0 | 0 | 0 | 0 | 0 | 0 | 0 |
| Cyclohexane aminomethane | 74 | 70 | 80 | 78 | 78 | 74 | 54 | 55 | 60 | 67 | 52 |
| Tranexamic acid | 73 | 79 | 80 | 80 | 78 | 75 | 68 | 68 | 65 | 75 | 58 |
| Cetraxate hydrochloride | 72 | 80 | 80 | 70 | 75 | 70 | 54 | 58 | 54 | 70 | 48 |
| Rotraxate hydrochloride | 80 | 84 | 86 | 74 | 76 | 75 | 62 | 59 | 53 | 75 | 56 |
| Benzylamine | 70 | 68 | 78 | 80 | 80 | 76 | 48 | 52 | 54 | 68 | 49 |
| p-Aminomethyl benzoic acid | 76 | 74 | 85 | 84 | 80 | 72 | 60 | 65 | 58 | 70 | 54 |
| Mafenide acetate | 67 | 52 | 74 | 78 | 75 | 70 | 56 | 59 | 55 | 66 | 32 |
| Dopamine hydrochloride | 64 | 52 | 72 | 77 | 70 | 72 | 50 | 55 | 60 | 50 | 29 |

As shown in Table 3, a trypsin-like enzyme has a relatively high activity in human nasal mucosal homogenate, while plasmin has a considerably low activity. However, there were some substrates corresponding to trypsin (in Table 3, Bz-Arg-MCA) which do not cleave much at all. Also, it became clear that the enzyme present in the human nasal mucosal homogenate is not trypsin itself. That is, it is guessed that in the human nasal cavity, peptide proteinaceous drugs are mainly cleaved down by enzymes which are not trypsin, but have trypsin-like activity.

Reference Experiment 3

A homogenate solution was prepared from human nasal mucosa to give 1 mg/ml of protein. Next, 0.25 ml portions of aqueous solutions (72 mM) of the different peptide proteinaceous drugs were added to 0.5 ml portions of the homogenate solution, 0.01 ml portions of aqueous solutions (72M) of different enzyme inhibitors or absorption acceler- The Aprotinin, Gabexate, ACA, and Tranexamic acid used were made by Wako Pure Chemical Industry, chymostatin was made by the Peptide Kenkyusho, TPCK and Thiorphan were made by Sigma Co., Pepstatin was made by Boehringer Mannheim Co., cetraxate hydrochloride was made by Daiichi Pharmaceutical Co., the rotraxate hydrochloride was synthesized and refined based on the description of Japanese Examined Patent Publication (Kokoku) No. 60-36418, the mafenide acetate was made by Tokyo Kasei Co., and the dopamine hydrochloride was made by Wako Pure Chemical Industry. Furthermore the benzylamine was made by Wako Pure Chemical Industry and the p-aminomethyl benzoic acid was made by Tokyo Kasei Co.

As shown in Table 4, it is clear that by including a trypsin inhibitor, the degradation of the peptide proteinaceous drug in the human nasal mucosal homogenate is obstructed. More surprisingly, it became clear that tranexamic acid, which is not a trypsin inhibitor, and other compounds of the present invention which are not trypsin inhibitors and are also not recognized as enzyme inhibitors, such as cyclohexane methylamine, cetraxate hydrochloride, rotraxate hydrochloride, benzylamine, p-aminomethyl benzoic acid, mafenide acetate, dopamine hydrochloride, etc. have a function of inhibiting the degradation of peptide proteinaceous drugs higher than the trypsin inhibitors of aprotinin and gabexate mesylate (Gabexate). This function is not observed in 6-amino caproic acid ($\epsilon$-ACA), so it is clear that it is not an inhibition function of plasmin. In other words, it is guessed that the enzymes which cleave peptide proteinaceous drugs in human nasal cavities are trypsin-like enzymes having the characteristic of being remarkably restrained in activity by compounds of the present invention like tranexamic acid, cyclohexane methylamine, rotraxate hydrochloride, cetraxate hydrochloride, benzylamine, p-aminomethyl benzoic acid, mafenide acetate, and dopamine hydrochloride.

Example 1

Figure 1:
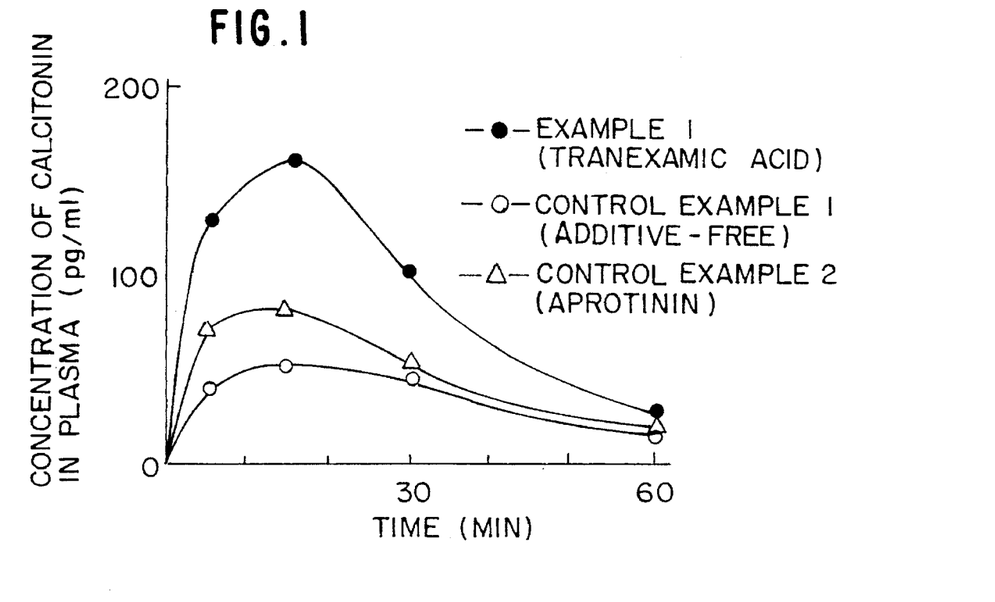
FIG. 1 is a graph showing the changes along with time of the concentration of salmon calcitonin in the plasma in normal human volunteers after administration of a calcitonin nasal powder composition.

Salmon calcitonin in an amount of 40 µg, tranexamic acid 40 µg, microcrystalline cellulose 30 mg, and magnesium stearate 15 µg were mixed in a mortar to prepare a tranexamic acid-added calcitonin nasal powder. The powder was weighed to give 100 IU (20 µg) of calcitonin, was packed in No. 2 capsules, then was administered to the right nasal cavities of three normal human volunteers by a Publizer (registered trademark, Teijin). After administration, 5 ml of blood was taken from a vein in the forearm every certain period and the concentration of salmon calcitonin in the plasma was measured by the RIA method. The results are shown in FIG. 1 by the time curve of the concentration of salmon calcitonin in the plasma.

Control Example 1

The same procedure was followed as in Example 1, except that 40 µg of tranexamic acid was not added, to prepare a tranexamic acid-free calcitonin nasal powder, the powder was weighed to give 100 IU (20 µg) of calcitonin and was packed in No. 2 capsules, then was administered to three normal human volunteers in the same way as in Example 1, then after a certain time the concentration of salmon calcitonin in the plasma was measured. The results are shown together in FIG. 1.

Control Example 2

The same procedure was followed as in Example 1, except that use was made of 0.4 mg of aprotinin instead of the 40 µg of tranexamic acid in Example 1, to prepare an aprotinin-added calcitonin nasal powder, the powder was administered to three normal human volunteers in the same way as in Example 1, then after a certain time the concentration of salmon calcitonin in the plasma was measured. The results are shown together in FIG. 1.

Example 2

Figure 2:
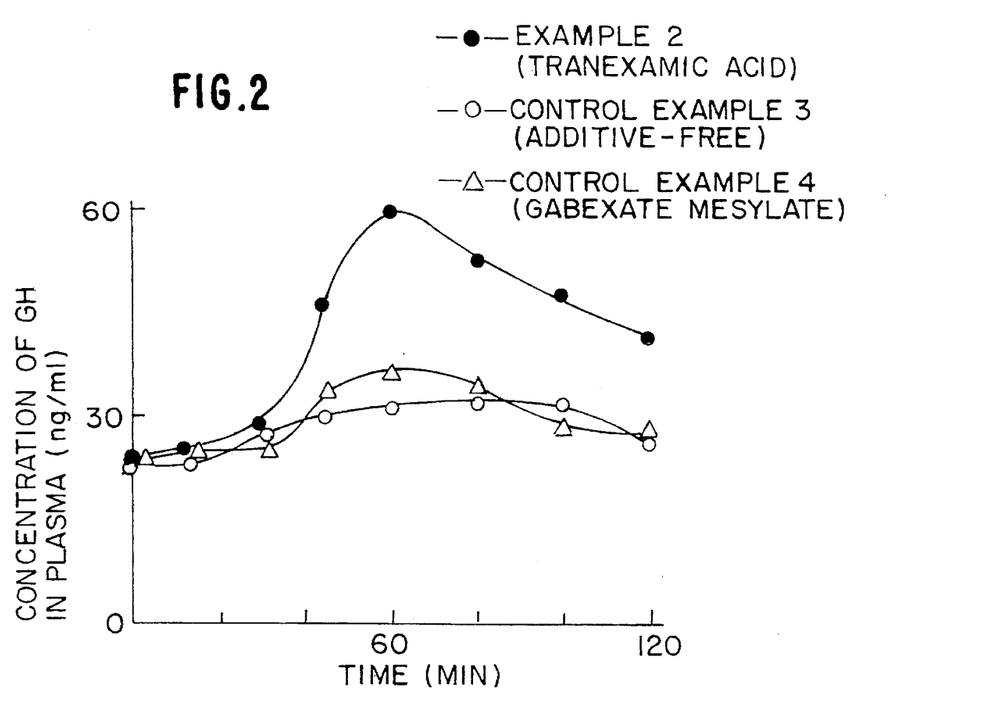
FIG. 2 is a graph showing the changes along with time of the concentration of GH in the plasma in normal human volunteers after administration of a GHRH nasal powder composition.

Somatorein acetate (GHRH) in an amount of 2.0 mg, tranexamic acid 1.0 mg, microcrystalline cellulose 30 mg, and magnesium stearate 15 µg were mixed in a mortar to prepare a tranexamic acid-added GHRH nasal powder. The powder was weighed to give a 1.0 mg amount of GHRH, was packed in No. 2 capsules, and was administered to the right nasal cavities of three normal human volunteers in the same way as in Example 1, then after a certain time the concentration of growth hormone (GH) in the plasma was measured. The results are shown together in FIG. 2 by the time curve of the concentration of GH in the plasma.

Control Example 3

The same procedure was followed as in Example 2, except that 1.0 mg of tranexamic acid was not added, to prepare a tranexamic acid-free GHRH nasal powder, the powder was weighed to give 1.0 mg of GHRH and was packed in No. 2 capsules, then was administered to three normal human volunteers in the same way as in Example 2, then after a certain time the concentration of GH in the plasma was measured. The results are shown together in FIG. 2.

Control Example 4

The same procedure was followed as in Example 2, except that use was made of 2.0 mg of gabexate mesylate instead of 1.0 mg of tranexamic acid, to prepare a gabexate mesylate-added GHRH nasal powder, the powder was administered to three normal human volunteers in the same way as in Example 2, then after a certain time the concentration of GH in the plasma was measured. The results are shown together in FIG. 2.

Example 3

Figure 3:
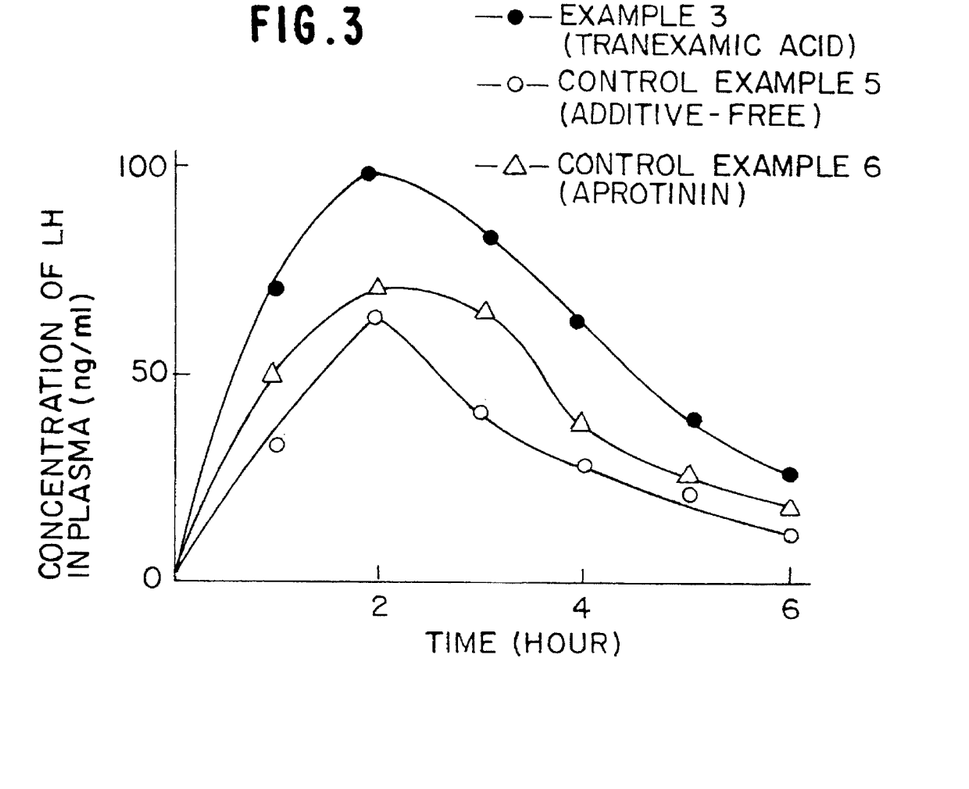
FIG. 3 is a graph showing the changes along with time of the concentration of LH in the plasma in normal human volunteers after administration of an LHRH nasal powder composition.

Deslorelin (LHRH derivative) in an amount of 0.2 mg, tranexamic acid 0.2 mg, microcrystalline cellulose 30 mg, and magnesium stearate 15 µg were mixed in a mortar to prepare a tranexamic acid-added LHRH derivative nasal powder. The powder was weighed to give 1.0 mg of the LHRH derivative, was packed in No. 2 capsules, then was administered to the right nasal cavities of three normal human volunteers in the same way as in Example 1, then after a certain time the concentration of leuteinizing hormone (LH) in the plasma was measured. The results are shown in FIG. 3 by the time curve of the LH concentration in the plasma.

Control Example 5

The same procedure was followed as in Example 3, except that 0.2 mg of tranexamic acid was not added, to prepare a tranexamic acid-free LHRH derivative nasal powder, the powder was weighed to give 1.0 mg of LHRH derivative and was packed in No. 2 capsules, then was administered to three normal human volunteers in the same way as in Example 3, then after a certain time the concentration of GH in the plasma was measured. The results are shown together in FIG. 3.

Control Example 6

The same procedure was followed as in Example 3, except that use was made of 0.4 mg of aprotinin instead of 0.2 mg of tranexamic acid, to prepare an aprotinin-added LHRH derivative nasal powder, the powder was administered to three normal human volunteers in the same way as in Example 3, then after a certain time the concentration of LH in the plasma was measured. The results are shown in FIG. 3.

Example 4

Figure 4:
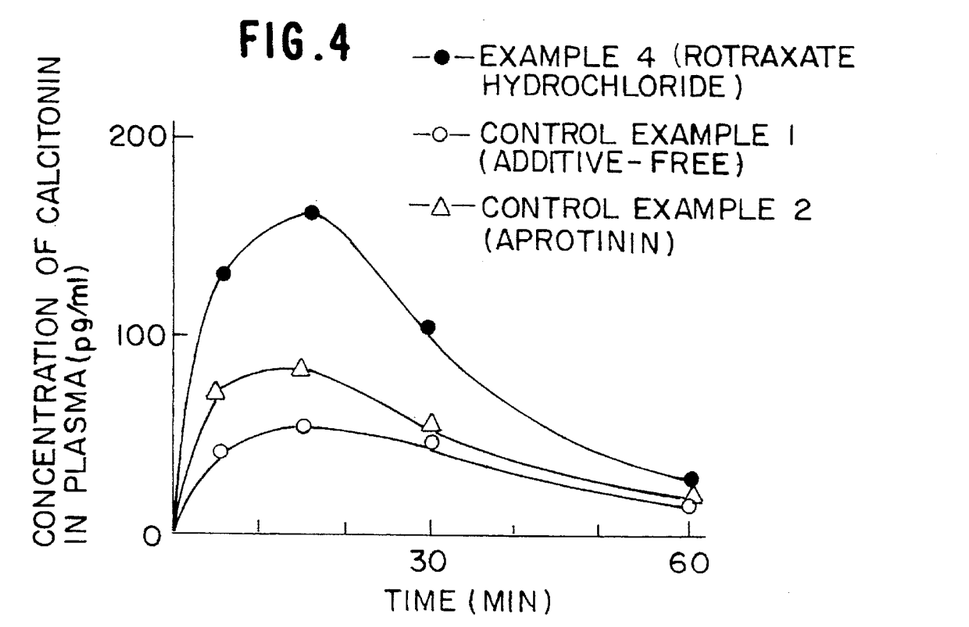
FIG. 4 is a graph showing the changes along with time of the concentration of salmon calcitonin in the plasma in normal human volunteers in Example 4 after administration of a calcitonin nasal powder composition.

Salmon calcitonin in an amount of 40 µg, rotraxate hydrochloride 40 µg, microcrystalline cellulose 30 mg, and magnesium stearate 15 µg were mixed in a mortar and mix to prepare a rotraxate hydrochloride-added calcitonin nasal powder. The powder was weighed to give 100 IU (20 µg) of calcitonin and was packed in No. 2 capsules, then was administered in the right nasal cavity of three normal human volunteers by a Publizer (registered trademark, Teijin). After administration, 5 ml of blood was taken from a vein in the forearm every certain period and the concentration of salmon calcitonin in the plasma was measured by the RIA method. The results are shown in FIG. 4 by the time curve of the concentration of salmon calcitonin in the plasma together with the results of Comparative Examples 1 and 2.

Example 5

Figure 5:
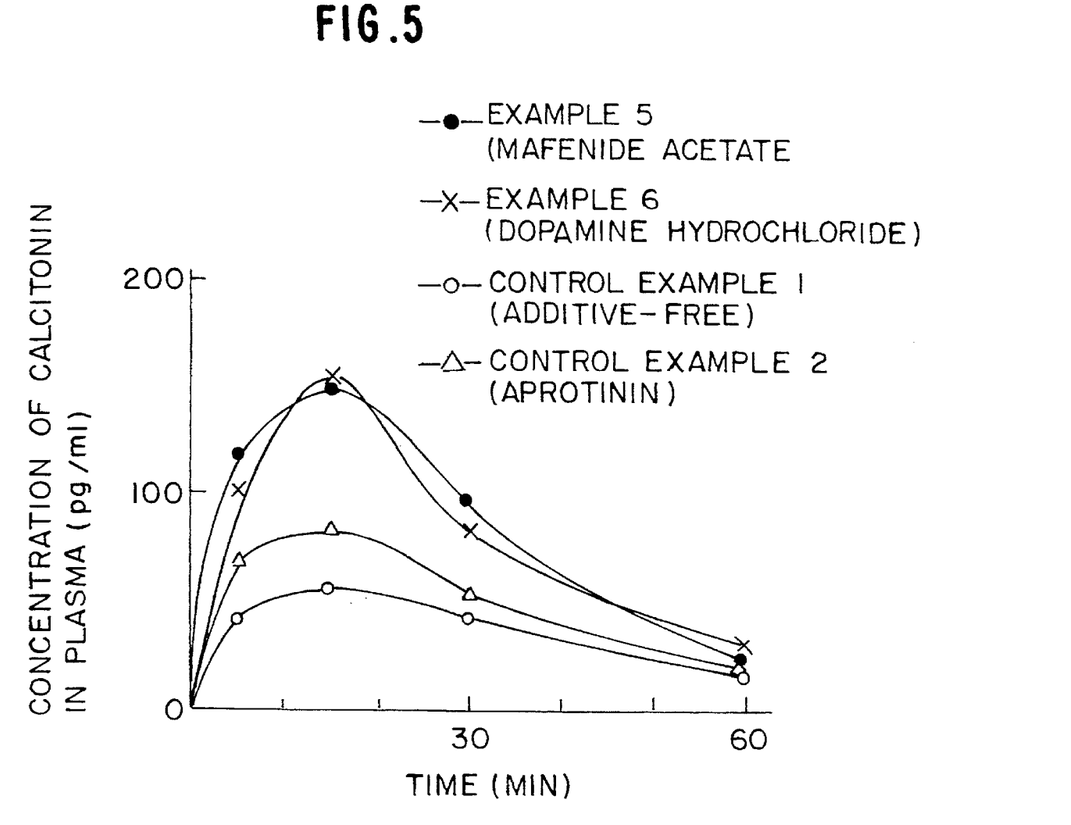
FIG. 5 shows the concentration of calcitonin in the plasma in the case of administration of nasal preparations of the present invention in Examples 5 and 6 and nasal preparations in Control Examples 1 and 2.

Salmon calcitonin in an amount of 40 μg, mafenide acetate 60 μg, microcrystalline cellulose 30 mg, and magnesium stearate 15 μg were mixed in a mortar to prepare a mafenide acetate-added calcitonin nasal powder. The powder was weighed to give 100 IU (20 μg) of calcitonin and was packed in No. 2 capsules, then was administered in the right nasal cavity of three normal human volunteers by a Publizer (registered trademark). After administration, 5 ml of blood was taken from a vein in the forearm every certain period of 5 minutes, 15 minutes, 30 minutes, and 60 minutes, and the concentration of salmon calcitonin in the plasma was measured by the RIA method. The results are shown in FIG. 5 by the time curve of the concentration of salmon calcitonin in the plasma.

Example 6

The same procedure was followed as in Example 5, except that use was made of 50 μg of dopamine hydrochloride instead of 60 μg of mafenide acetate, to prepare a dopamine hydrochloride-added calcitonin nasal powder. The powder was weighed to give 100 IU (20 μg) of calcitonin and was packed in No. 2 capsules, then was administered to three normal human volunteers in the same way as in Example 5, then after a certain time the concentration of salmon calcitonin in the plasma was measured. The results are shown together with the results of the above-mentioned Comparative Examples 1 and 2 in FIG. 5.

INDUSTRIAL APPLICABILITY

According to the present invention, there is provided a peptide proteinaceous drug nasal powder composition which is improved in absorbency and a peptide proteinaceous drug nasal powder composition which is improved in absorbency and safe to the body.

---

We claim:

1. A peptide proteinaceous drug nasal powder composition comprising (i) an absorption accelerant comprising a compound, or its salt, having in the compound molecule a group expressed by the formula (II):

wherein, represents a cyclohexane ring or a benzene ring; n is an integer of 1 or 2; $R^1$, $R^2$ and $R^3$ are, independently, a member selected from the group consisting of a hydrogen atom -COOR, -COR, -OR', and -$SO_2NH_2$, which may be substituted; provided that at least one of $R^1$, $R^2$ or $R^3$ is a hydrogen atom; R represents a hydrogen atom, a $C_1$–$C_6$ lower alkyl group which may be substituted, or $CH_2CH_2COOR'$; R' represents a hydrogen atom, a $C_1$–$C_6$ lower alkyl group which may be substituted, a phenyl group which may be substituted, or a $C_7$–$C_8$ aralkyl group which may be substituted, and (ii) a therapeutically effective amount of a peptide proteinaceous drug.

2. A nasal powder composition as set forth in claim 1, wherein in formula (II) is a cyclohexane ring and n=1.

3. A nasal powder composition as set forth in claim 2, wherein the cyclohexane ring is substituted by a member selected from the group consisting of a hydrogen atom, -CO-$C_6H_5$-$(CH_2)_2$COOH, a carboxyl group, and -COO-$C_6H_5$-$(CH_2)_2$COOH.

4. A nasal powder composition as set forth in claim 2, wherein $R^1$ and $R^3$ in formula (II) are each a hydrogen atom and $R^2$ is -COO -CH$_6$H$_5$-(CH$_2$)$_2$COOH.

5. A nasal powder composition as set forth in claim 2, wherein $R^1$ and $R^3$ in formula (II) are each a hydrogen atom and $R^2$ is -CO-C$_6$H$_5$-(CH$_2$)$_2$-COOH.

6. A nasal powder composition as set forth in claim 2, wherein $R^1$ and $R^3$ in formula (II) are each a hydrogen atom and $R^2$ is a carboxyl group.

7. A nasal powder composition as set forth in claim 1 wherein in formula (II) is a benzene ring.

8. A nasal powder composition as set forth in claim 7, wherein the benzene ring is substituted by a member selected from the group consisting of a hydrogen atom, a carboxyl group, a hydroxyl group and a sulfamine group.

9. A nasal powder composition as set forth in claim 7, wherein $R^1$ and $R^3$ in formula (II) are each a hydrogen atom, $R^2$ is a carboxyl group and n is 1.

10. A nasal powder composition as set forth in claim 7, wherein $R^1$ and $R^3$ in formula (II) are each a hydrogen atom, $R^2$ is a sulfamine group, and n is 1.

11. A nasal powder composition as set forth in claim 7, wherein, in formula (II), $R^1$ is a hydrogen atom, $R^2$ and $R^3$ are each a hydroxyl group, and n is 2.

12. A nasal powder composition as set forth in claim 1, wherein the peptide proteinaceous drug is at least one peptide proteinaceous drug selected from the group consisting of calcitonins, insulins, somatostatin (GIF)and derivatives thereof, parathyroid hormones (PTH), substance P, platelet derived growth factors (PDGF), galanin, gastrin, neurokinins, interleukins, neurotensin, endo serine, growth hormones (GH), growth hormone-releasing hormone (GHRH) and derivatives thereof, growth hormone releasing factor (GRF), luteinizing hormone-releasing hormone (LHRH) and derivative thereof, enkephalin and derivatives thereof, secretin, bradykinin and derivatives thereof, adrenocorticotrophic hormone (ACTH) and derivatives thereof, glucagon, insulin growth factor (IGF), calcitonin gene related peptide (CCRP) interferons, vasopressin and derivatives thereof, atrial natrium peptide (ANP), erythropoietin, and granulocyte colony stimuli factor (G-CSF).

13. A nasal powder composition as set forth in claim 1, wherein the peptide proteinaceous drug is at least one peptide proteinaceous drug selected from the group consisting of calcitonins, insulins, somatostatin (GIF) and derivatives thereof, parathyroid hormones (PTH), substance P, platelet derived growth factors (PDGF), growth hormone-releasing hormone (GHRH) and derivatives thereof, luteinizing hormone-releasing hormone (LHRH) and derivatives thereof, adrenocorticotrophic hormone (ACTH) and derivatives thereof, glucagon, and calcitonin gene related peptide (CGRP).

14. A nasal powder composition as set forth in claim 1, wherein the peptide proteinaceous drug is at least one peptide proteinaceous drug selected from the group comprising salmon, eel, human, pig, and chicken natural calcitonin and derivatives thereof.

15. A nasal powder composition as set forth in claim 1, wherein the peptide proteinaceous drug is at least one peptide proteinaceous drug selected from the group consisting of human, rat, and pig natural somatostatin and derivatives thereof.

16. A nasal powder composition as set forth in claim 1, wherein the peptide proteinaceous drug is at least one peptide proteinaceous drug selected from the group consisting of bovine, human, and rat natural parathyroid hormone (PTH) and derivatives thereof.

17. A nasal powder composition as set forth in claim 1, wherein the peptide proteinaceous drug is at least one peptide proteinaceous drug selected from the group consisting of bovine, human, rat, and pig natural luteinizing hormone-releasing hormone (LHRH) and derivatives thereof.

18. A nasal powder composition as set forth in claim 1, wherein the peptide proteinaceous drug is at least one peptide proteinaceous drug selected from the group consisting of human, rat, and pig natural growth hormone-releasing hormone (GHRH) and derivatives thereof.

* * * * *